United States Patent
Tominaga et al.

(10) Patent No.: US 12,044,642 B2
(45) Date of Patent: Jul. 23, 2024

(54) METHOD AND DEVICE FOR ESTIMATING OUTER SURFACE TEMPERATURE OF RADIANT COIL OF CRACKING FURNACE FOR ETHYLENE PRODUCTION AND ETHYLENE PRODUCING DEVICE

(71) Applicant: TOYO ENGINEERING CORPORATION, Tokyo (JP)

(72) Inventors: Kenichi Tominaga, Narashino (JP); Michiko Nakajo, Narashino (JP); Noritaka Sakaguchi, Narashino (JP)

(73) Assignee: TOYO ENGINEERING CORPORATION, Tokyo (JP)

( * ) Notice: Subject to any disclaimer, the term of this patent is extended or adjusted under 35 U.S.C. 154(b) by 742 days.

(21) Appl. No.: 17/302,018

(22) Filed: Apr. 21, 2021

(65) Prior Publication Data

US 2021/0239633 A1    Aug. 5, 2021

Related U.S. Application Data

(63) Continuation of application No. PCT/JP2019/038736, filed on Oct. 1, 2019.

(30) Foreign Application Priority Data

Nov. 2, 2018    (JP) ................. 2018-207772

(51) Int. Cl.
*G01N 25/72*    (2006.01)
*C07C 4/04*    (2006.01)
(Continued)

(52) U.S. Cl.
CPC ............... *G01N 25/72* (2013.01); *C07C 4/04* (2013.01); *G01J 5/48* (2013.01); *C07C 11/04* (2013.01)

(58) Field of Classification Search
CPC . G01N 25/72; C07C 4/04; C07C 11/04; G01J 5/48
(Continued)

(56) References Cited

U.S. PATENT DOCUMENTS

| 2009/0020459 A1 | 1/2009 | De et al. |
| 2018/0275690 A1 | 9/2018 | Lattanzio et al. |

FOREIGN PATENT DOCUMENTS

| CA | 2789642 A1 * | 3/2014 | ............. F23N 3/002 |
| CN | 1259981 | 7/2000 | |

(Continued)

OTHER PUBLICATIONS

17302018_2024-03-19_CA_2789642_A1_H.pdf, Mar. 14, 2014.*
(Continued)

*Primary Examiner* — Gail Kaplan Verbitsky
(74) *Attorney, Agent, or Firm* — Schwegman Lundberg & Woessner, P.A.

(57) ABSTRACT

A device for estimating an outer surface temperature of a radiant coil which is provided in an cracking furnace for ethylene production including a convection coil that preheats hydrocarbons as raw materials and steam, a radiant coil that thermally decomposes the preheated hydrocarbons and steam, and a housing for accommodating them, and which includes an imaging camera that images a region to be imaged of the radiant coil, and an image analyzer that processes an output signal from the imaging camera and estimates an outer surface temperature of the radiant coil.

12 Claims, 5 Drawing Sheets

(51) Int. Cl.
  *G01J 5/48* (2022.01)
  *C07C 11/04* (2006.01)
(58) Field of Classification Search
  USPC .................................... 374/120, 121, 5, 57
  See application file for complete search history.

(56) References Cited

FOREIGN PATENT DOCUMENTS

| | | | |
|---|---|---|---|
| CN | 1503732 | | 6/2004 |
| CN | 101504249 A | * | 8/2009 |
| CN | 101679879 | | 3/2010 |
| CN | 107367331 A | | 11/2017 |
| CN | 107990986 A | | 5/2018 |
| EA | 031531 | | 1/2019 |
| JP | 05107116 A | | 4/1993 |
| JP | 07268356 A | | 10/1995 |
| JP | H1051758 A | * | 2/1998 |
| JP | 11263982 | | 9/1999 |
| JP | 2006518464 A | | 8/2006 |
| JP | 2015083677 A | | 4/2015 |
| RU | 2374454 | | 11/2009 |
| RU | 91144 | | 1/2010 |
| SU | 1033177 A1 | * | 8/1983 |
| WO | WO-2004069547 A2 | | 8/2004 |
| WO | WO-2007089742 A1 | * | 8/2007 ........... G01J 5/0014 |
| WO | WO-2008137932 A1 | * | 11/2008 ........... A61B 5/0071 |
| WO | 2018104695 | | 6/2018 |

OTHER PUBLICATIONS

17302018_2024-03-19_CN_101504249_A_H.pdf, Aug. 12, 2009.*
17302018_2024-03-19_SU_1033177_A1_H.pdf, Aug. 7, 1983.*
17302018_2024-03-19_WO_2007089742_A1_H.pdf, Aug. 9, 2007.*
17302018_2024-03-19_WO_2008137932_A1_H.pdf, Nov. 13, 2008.*
17302018_2024-03-19_JP_H1051758_A_H.pdf, Feb. 20, 1998.*
"Egyptian Application Serial No. 639 2021, Office Action dated Mar. 14, 2023", w English Translation, (Mar. 14, 2023), 9 pgs.
"International Application Serial No. PCT/JP2019/038736, International Preliminary Report on Patentability mailed Oct. 30, 2020", w/ English Claims, (Oct. 30, 2020), 12 pgs.
"International Application Serial No. PCT/JP2019/038736, International Search Report mailed Dec. 17, 2019", w/ English Translation, (Dec. 17, 2019), 5 pgs.
"International Application Serial No. PCT/JP2019/038736, Written Opinion mailed Dec. 17, 2019", (Dec. 17, 2019), 5 pgs.
"Russian Application Serial No. 2021114053, Office Action dated Oct. 19, 2022", w English Translation, (Oct. 19, 2022), 14 pgs.
"Chinese Application No. 201980070455.1, Office Action dated Mar. 26, 2024", w English Translation, (Mar. 26, 2024), 11 pgs.

* cited by examiner

METHOD AND DEVICE FOR ESTIMATING OUTER SURFACE TEMPERATURE OF RADIANT COIL OF CRACKING FURNACE FOR ETHYLENE PRODUCTION AND ETHYLENE PRODUCING DEVICE

CLAIM FOR PRIORITY

This application is a continuation of International Application No. PCT/JP2019/038736, filed Oct. 1, 2019, which claims priority to Japanese Patent Application No. 2018-207772, filed Nov. 2, 2018, each of which is incorporated herein by reference in their entireties.

TECHNICAL FIELD

The present invention relates to a method and device for estimating a temperature of an outer surface of a radiant coil of an cracking furnace for ethylene production and an ethylene producing device including the estimating device.

BACKGROUND ART

In this type of cracking furnace for ethylene production, raw materials including hydrocarbons such as naphtha and steam are supplied to a plurality of coils, a fluid mixture is preheated in a convection section, and then the naphtha and the like are thermally decomposed at 750 to 900° C. in a radiant section, and thereby olefins such as ethylene and propylene are produced as main products.

Coils are generally tubes made of a heat-resistant alloy having a diameter of about 20 mm to 180 mm and a length of about 10 m to 100 m. As the operating time of an cracking furnace for ethylene production increases, coke as a by-product gradually accumulates on the inner surface thereof. An cracking furnace for ethylene production is controlled so that an outlet temperature of the coil is adjusted in order to keep the yield of olefins at a predetermined value. Therefore, when coke accumulates on the inner surface of the coil, the outer surface temperature of the coil gradually increases when it becomes a coke layer and inhibits heat conduction through the tube wall. Before the outer surface temperature of the coil reaches a design temperature of the heat-resistant alloy, it is necessary to stop the cracking furnace for ethylene production, perform decoking, and combust and remove the coke adhered to the coil.

In the related art, as described in Patent Literature 1, in order to determine the decoking time, an observation window provided in the cracking furnace for ethylene production is opened, and the outer surface temperature of the coil is regularly measured manually with a pyrometer (non-contact thermometer that detects infrared radiation). when the measured outer surface temperature approaches the design temperature of the heat-resistant alloy to some extent, the supply of hydrocarbons as raw materials is stopped and the coil is decoked.

CITATION LIST

Patent Literature

[Patent Literature 1]
Japanese Unexamined Patent Application, First Publication No. H7-268356

SUMMARY OF INVENTION

Technical Problem

In this type of cracking furnace for ethylene production, coke does not accumulate uniformly inside all the coils, and the coke may start to adhere relatively more thickly at arbitrary portions of arbitrary coils due to variation in the decomposition reactions. Then, the temperature increases locally at such portions, additional coke accumulation proceeds, and a relatively high temperature region (hotspot) is generated.

However, in the temperature measurement method using a pyrometer as in Patent Literature 1, since the temperature measurement region is narrowed down to almost one point, even if a relatively high temperature portion is locally generated outside the temperature measurement region, there are problems of the temperature not being easily reflected in the measurement results, and local heating being easily overlooked.

Solution to Problem

[1] A method for estimating an outer surface temperature of a radiant coil of an cracking furnace for ethylene production according to the present invention is a method for estimating an outer surface temperature of a radiant coil of an cracking furnace for ethylene production including a convection section coil that preheats hydrocarbons as raw materials and steam, a radiant coil that thermally decomposes the preheated hydrocarbons and steam, and a housing for accommodating them, the method including a process in which a region to be imaged of the radiant coil is imaged by an imaging camera and a process in which an output signal from the imaging camera is processed by an image analyzer and an outer surface temperature of the radiant coil is estimated.

[2] In the method of [1], the region to be imaged by the imaging camera may be a region that spans a plurality of radiant coils.

[3] In the method of [1] or [2], the image analyzer may estimate a maximum temperature in the region to be imaged.

[4] In the above [1] to [3], the image analyzer may process the output signal from the imaging camera, identify a hotspot in the region to be imaged, and output a hotspot temperature in the hotspot. In this case, since the imaging camera can find a hotspot in a relatively large region to be imaged and estimate a hotspot temperature thereof, a likelihood of coke accumulation proceeding in the hotspot being overlooked is small, and it is possible to prevent a problem of the outer surface temperature of the radiant coil locally exceeding a design temperature.

[5] In the above [1] to [4], the outer surface temperature of the radiant coil at any position estimated by the image analyzer is displayed on a display device together with the estimated position information. In a conventional method of measuring a temperature by a pyrometer, it is difficult to accurately determine a position at which a hotspot has occurred in the radiant coils. However, according to the method, since it is possible to visually confirm a position at which a hotspot has occurred in the radiant coils, and a trend can be understood by collecting hotspot appearance positions and appearance frequency information, this can be effectively used as information for determining a decoking time and maintenance.

[6] A device for estimating an outer surface temperature of a radiant coil of an cracking furnace for ethylene production according to the present invention is provided in an cracking furnace for ethylene production including a convection coil that preheats hydrocarbons as raw materials and steam, a radiant coil that thermally decomposes the preheated hydrocarbons and steam, and a housing for accommodating them, and the estimating device includes an imaging camera that images a region to be imaged of the radiant coil; and an image analyzer that processes an output signal from the imaging camera and estimates an outer surface temperature of the radiant coil.

[7] In the device of [6], the region to be imaged by the imaging camera may be a region of the radiant coil that spans a plurality of radiant coils.

[8] In the device of [6] or [7], the image analyzer may include a maximum temperature estimating unit that estimates a maximum temperature in the region to be imaged.

[9] In the device of [8], the image analyzer may include a hotspot identification unit that processes the output signal from the imaging camera and identifies a hotspot in the region to be imaged and a hotspot temperature calculation unit that calculates a hotspot temperature in the hotspot. In this case, since the hotspot identification unit finds a hotspot in a relatively large region to be imaged, and a hotspot temperature thereof is calculated by the hotspot temperature calculation unit, this helps to reduce the oversight of coke accumulation proceeding in the hotspot being overlooked, and it is possible to prevent a problem of the outer surface temperature of the radiant coil locally exceeding a design temperature.

[10] In the above [7] to [9], the outer surface temperature of the radiant coil at any position estimated by the image analyzer may be displayed on a display device together with the estimated position information. In this case, since it is possible to visually confirm a position at which a hotspot has occurred in the radiant coils, and a trend of the hotspot appearance position and appearance frequency can be understood, this can be effectively used as information for determining a decoking time and maintenance.

[11] An ethylene producing device according to the present invention including the device for estimating an outer surface temperature of a radiant coil of an cracking furnace for ethylene production according to any one of [6] to [10], the ethylene producing device including an cracking furnace for ethylene production including a convection coil that preheats hydrocarbons as raw materials and steam, a radiant coil that thermally decomposes the preheated hydrocarbons and steam, and a housing for accommodating them.

Advantageous Effects of Invention

According to the method and device for estimating an outer surface temperature of a radiant coil of an cracking furnace for ethylene production according to the present invention, when an imaging camera images a region to be imaged of the radiant coil, and an image analyzer processes an output signal from the imaging camera, it is possible to estimate an outer surface temperature of the radiant coil corresponding to the region to be imaged and even if there is a relatively high-temperature portion in the region to be imaged, it is possible to estimate an outer surface temperature of the radiant coil by reflecting the temperature in the high-temperature portion.

An ethylene producing device according to the present invention includes a device for estimating an outer surface temperature of a radiant coil of an cracking furnace for ethylene production. Therefore, even if there is a relatively high-temperature portion in the region to be imaged, since it is possible to estimate an outer surface temperature of the radiant coil by reflecting the temperature in the high-temperature portion, and it is possible to perform decoking at an appropriate time, it is possible to improve production efficiency of ethylene.

DESCRIPTION OF EMBODIMENTS

Figure 1:
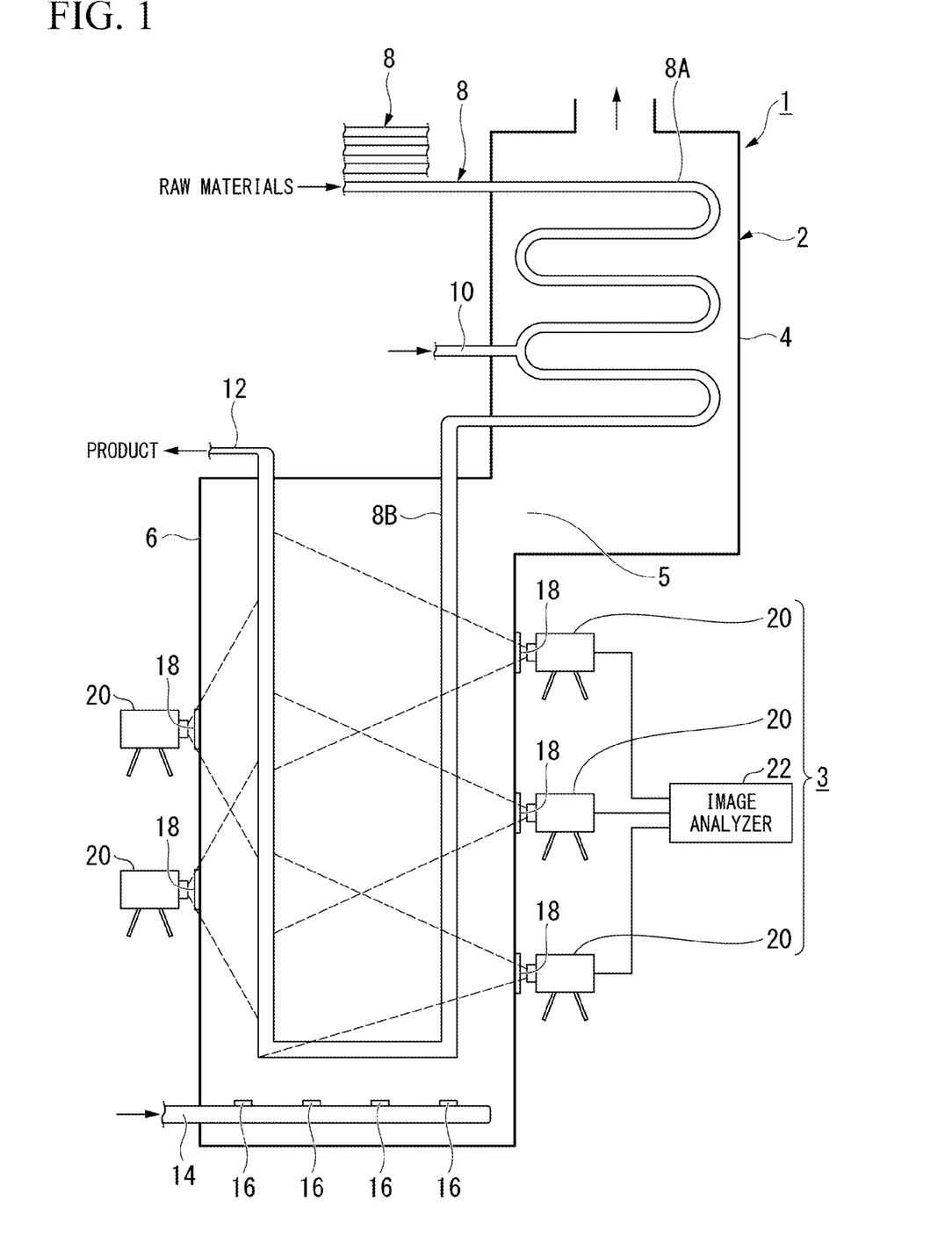
FIG. 1 is a schematic view showing an ethylene producing device including a device for estimating an outer surface temperature of radiant coil of an cracking furnace for ethylene production according to one embodiment of the present invention.

Hereinafter, embodiments according to the present invention will be described in detail. FIG. 1 is a schematic view of an ethylene producing device of the present embodiment, and the ethylene producing device includes an cracking furnace for ethylene production 1 that thermally decomposes hydrocarbon raw materials such as naphtha to produce ethylene and the like and a device for estimating an outer surface temperature of a radiant coil 3 of the cracking furnace for ethylene production 1. The cracking furnace for ethylene production 1 includes a control device (not shown), and various parameters of operating conditions are controlled by this control device.

[Cracking Furnace for Ethylene Production]

The cracking furnace for ethylene production 1 includes a coil 8 to which hydrocarbons as raw materials and steam are supplied, a convection section 4 that preheats a fluid mixture in the coil 8, a radiant section 6 that heats the coil 8 with radiant heat and thermally decomposes the raw materials, and a housing 2 for accommodating them. A part of the upper end of the radiant section 6 and a part of the lower end of the convection section 4 communicate with each other through a communication section 5, and heat of combustion in the radiant section 6 flows into the convection section 4 through the communication section 5. Therefore, it is designed such that the convection section 4 has a relatively low internal temperature suitable for preheating the raw materials in the coil 8 and the radiant section 6 has a relatively high internal temperature suitable for thermally decomposing the raw materials in the coil 8.

[Coil]

A plurality of coils 8 are provided, and are continuously arranged through the convection section 4, the outside of the communication section 5, and the radiant section 6. More specifically, a plurality of (for example, 4) coils 8 are inserted from the upper part of the convection section 4, and these plurality of convection coils 8A (only one is shown in FIG. 1) meander in the convection section 4 and reach downward. A steam introduction pipe 10 is connected to a part midway along the convection coil 8A, and high-temperature steam for dilution is introduced from steam supply source (not shown) to the convection coil 8A through the steam introduction pipe 10. A fluid mixture containing hydrocarbons as raw materials and steam is heated when it passes through the convection coil 8A.

A plurality of radiant coils 8B are connected to the downstream end of the convection coil 8A. The radiant coil 8B meanders up and down in the radiant section 6, and is connected to a delivery tube 12, and the delivery tube 12 extends outward from the upper part of the radiant section 6. The temperature of the fluid mixture preheated in the convection section 4 increases as the fluid mixture flows downward in the radiant coil 8B, raw material hydrocarbons are thermally decomposed, and ethylene and the like are produced. Although not limited, the diameter of the radiant coil 8B is, for example, about 20 mm to 180 mm, and the length thereof is, for example, about 10 m to 100 m.

The radiant coil 8B is preferably formed of a heat-resistant alloy such as a nickel-chromium alloy having excellent heat resistance. The design temperature in the cracking furnace for ethylene production 1 varies depending on the material of the coil, and although it is not limited, but is, for example, about 1,040° C. to 1,120° C.

A combustion nozzle 14 is installed in the lower part of the radiant section 6, and fuel and air are ejected upward from a plurality of nozzle holes 16 provided in the combustion nozzle 14 such that they combust in flames, and the radiant coil 8B is heated with the heat of combustion. Therefore, although not limited, the fluid mixture is heated to, for example, 750° C. to 900° C., before it reaches the outlet of the radiant coil 8B.

When coke accumulates on the inner surface of the radiant coil 8B, thermal resistance of the coke accumulation layer is additionally applied. Since the gas temperature at the outlet of the radiant coil 8B is controlled such that it has a constant temperature, the outer surface temperature of the radiant coil 8B becomes higher. Therefore, when coke accumulates, the outer surface temperature of the radiant coil 8B needs to be managed so that it does not exceed the design temperature. When coke accumulates and the outer surface temperature of the radiant coil 8B reaches the design temperature, since there is a risk of the strength and the lifespan of the radiant coil 8B decreasing, it is necessary to stop production of ethylene in the cracking furnace for ethylene production 1 and perform decoking. Decoking is performed by heating while sending air and steam in the coil 8 and combusting and removing coke.

The delivery tube 12 is also connected to a cooler (not shown), and the high-temperature decomposition product delivered from the delivery tube 12 is rapidly cooled to about 300° C. to 650° C., and prevents more decomposition production than necessary from proceeding. The thermal cracked product obtained in this manner is subjected to a multi-stage distillation column, and is fractionated and distilled into different components with respective boiling points, and many types of products including ethylene can be obtained.

[Imaging camera]

On the wall surface of the housing 2 in the radiant section 6, observation windows 18 are provided at a plurality of portions that face respective portions of the radiant coil 8B, and an imaging camera 20 is provided at a position at which each observation window 18 is looked into. The number of imaging cameras 20 and the positions thereof are not limited, and only one imaging camera may be installed to correspond to any of the observation windows 18 or the number of imaging cameras may be larger than that of the illustrated example (5 imaging cameras). Regarding the observation window 18, the observation window originally provided in the cracking furnace for ethylene production 1 may be used, or one may be newly provided for this estimating device.

The type of the imaging camera 20 is not particularly limited, and, for example, a monochromatic video camera, a color video camera, a 2-sensor camera, and the like can be used. In the case of a monochromatic video camera, the brightness for each light-receiving pixel at a single wavelength is output. In the case of a color video camera, for example, the brightness for each light-receiving pixel at each wavelength of RGB is output. In the case of a 2-sensor camera, the brightness for each light-receiving pixel at a wavelength A and a wavelength B is output.

Figure 2:
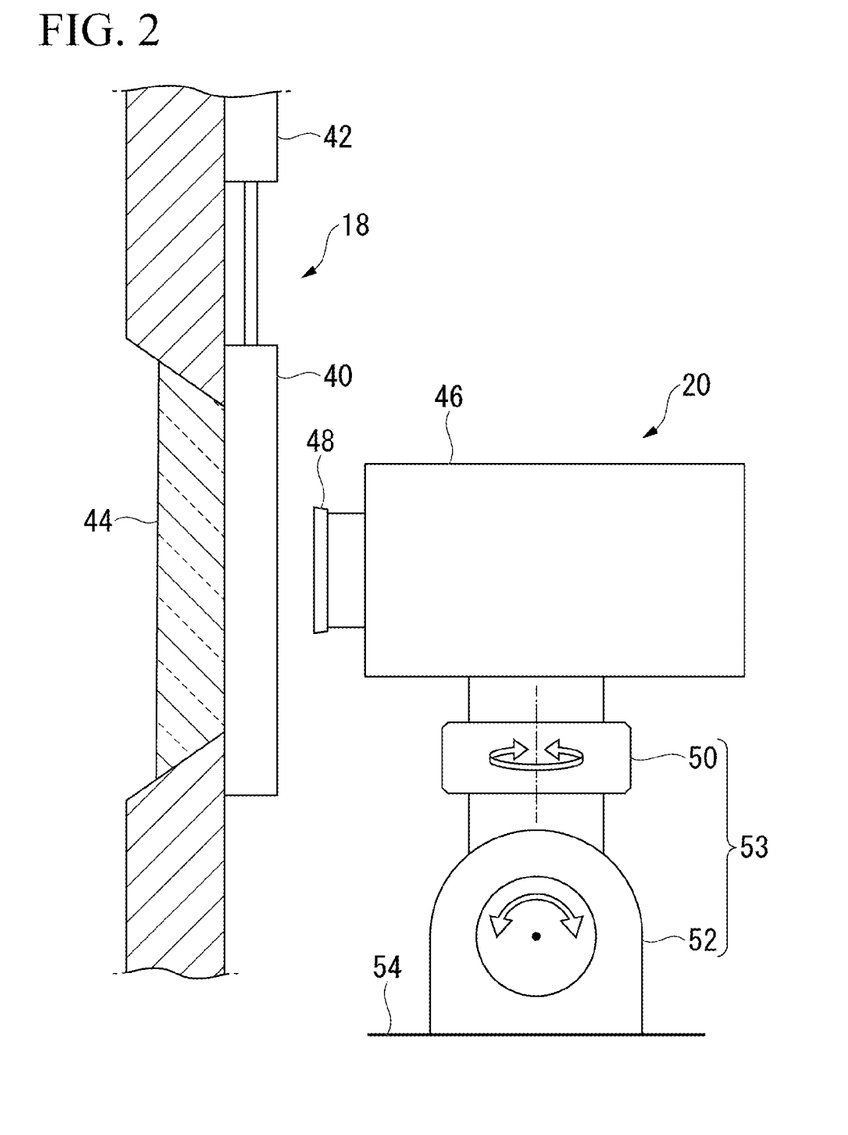
FIG. 2 is a side view showing an imaging camera of the same embodiment.

FIG. 2 is a side view showing an example of the observation window 18 and the imaging camera 20. The imaging camera 20 includes a camera main body 46 including an imaging sensor for measuring the brightness and a lens 48 for forming an image on the imaging sensor and is supported on a support stand 54 via a platform 53. The platform 53 includes a horizontal swivel unit 50 and a vertical swivel unit 52, and the orientation is adjusted by adjusting the units 50 and 52 and it is possible to image a region to be imaged of the desired radiant coil 8B through the observation window 18.

Figure 3:
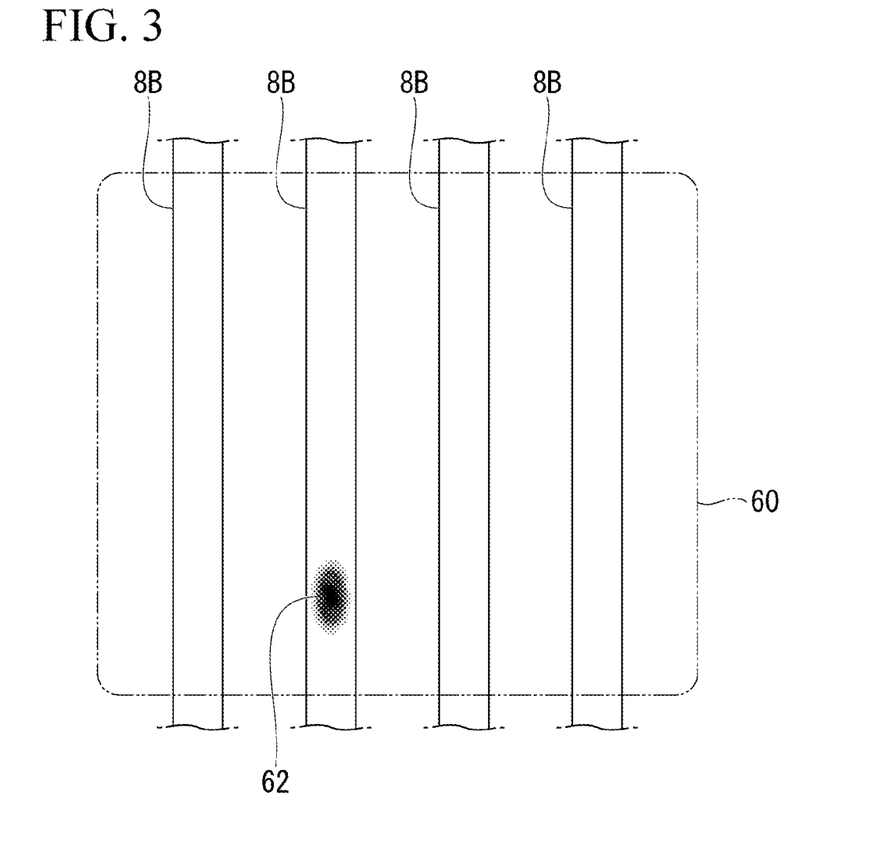
FIG. 3 is a front view showing a state in which a hotspot of a radiant coil is detected according to the same embodiment.

FIG. 3 shows an example of a region to be imaged 60 imaged by the imaging camera 20. In this example, the region to be imaged 60 has a rectangular shape, but the shape is not limited thereto, and as necessary, other shapes such as a circle or an ellipse may be used. It is desirable that the region to be imaged 60 include a part of the plurality of radiant coils 8B. If the region to be imaged 60 is wide, the possibility of a hotspot 62 being included therein increases. Even if the region to be imaged 60 does not include a hotspot, when a part of a relatively high-temperature region is included in the region to be imaged 60, it is possible to estimate the temperature by reflecting the temperature in the high-temperature range.

Although not necessarily limited, as shown in FIG. 1, the entire area of the radiant coil 8B positioned in the radiant section 6, and particularly, a downstream region (region in which flowing occurs from the lower side to the upper side in the drawing) in which coke tends to accumulate and the temperature tends to increase, is more preferably covered by the regions to be imaged 60 imaged by imaging cameras 20 without gaps. In this case, even if a hotspot occurs at any position in the downstream region, it is possible to detect the occurrence thereof.

As shown in FIG. 2, the observation window 18 of this embodiment includes a transparent window 44 made of a transparent heat-resistant material that closes an opening provided in the furnace wall, a shutter 40 that covers the outer surface of the transparent window 44 when imaging (temperature measurement) is not performed, and an actuator 42 that opens and closes the shutter 40. The actuator 42 opens the shutter 40 only when the imaging camera 20 performs imaging at regular intervals according to a program in a computer of a control system (not shown). When no imaging is performed, the shutter 40 is closed, and the thermal efficiency of the ethylene cracking furnace 1 is not lowered. The shutter 40 is not essential, and in some cases, it may be unnecessary for continuous imaging by the imaging camera 20, and it may have a configuration that opens and closes only when manual imaging is necessary.

Each of the imaging cameras 20 is connected to an image analyzer 22 for analyzing a signal output from the imaging camera 20 and outputting a temperature signal, and the image analyzer 22 is connected to a computer (not shown).

The image analyzer 22 receives an image output from the imaging camera 20 and analyzes the brightness from each point on the outer surface of the radiant coil 8B, and determines a temperature or the maximum temperature at any position in the field-of-view range of the imaging camera 20.

Various display devices (not shown) such as a liquid crystal display are connected to the computer, and the image analyzer 22 displays an image imaged by the imaging camera 20 and a position at which the hotspot 62 has occurred in the image on the display device, for example, as shown in FIG. 3. The image may be the image itself imaged by the imaging camera 20 or may be an image that can be recognized as a temperature distribution in which the captured image is schematically processed. Therefore, since it is possible to visually confirm a position at which a hotspot has occurred in the radiant coils 8B, and a trend can be understood by collecting hotspot appearance positions and appearance frequency information, this can be effectively used as information for determining a decoking time and maintenance.

The image analyzer 22 receives an image signal from the imaging camera 20 and continuously outputs a signal indicating the highest temperature in a field of view 61 at each time point. The computer (not shown) continuously receives the maximum temperature from the image analyzer 22, and stores the highest temperature estimated from the brightness during the scanning as the maximum temperature measured by the imaging camera 20 after scanning of the imaging camera 20 is completed. Therefore, since it is possible to detect a position at which the temperature of the outer surface of the radiant coils becomes a maximum with high accuracy, it is possible to predict the decoking time with higher accuracy.

In addition, instead of receiving only the maximum temperature as described above, a function of receiving temperature information at an arbitrary position together with position information, and, for example, outputting a temperature distribution diagram of outer surfaces of a plurality of radiantcoils may be included.

A method for estimating a temperature by the image analyzer 22 can be as follows, but is not limited in the present invention.

(1) Using a monochromatic video camera, the brightness of the outer surface of the radiant coil 8B at a single wavelength is measured, and an outer surface temperature is estimated from a calibration curve of the brightness and the outer surface temperature of the radiant coil 8B obtained in advance. In this case, when measurement conditions change, the estimated temperature is affected, but in the present embodiment, since the imaging camera is fixed, the change in measurement conditions is small, and even with a simple configuration using the monochromatic video camera, the outer surface temperature can be estimated relatively accurately. Although not limited, the single wavelength may be, for example, 1 to 3 μm, which is a black body radiation wavelength at 1,000° C. to 1,300° C.

(2) The brightness ratio between the first wavelength and the second wavelength is determined using a color video camera, a 2-sensor camera, or the like, and an outer surface temperature is estimated from the calibration curve of the brightness ratio between the first wavelength and the second wavelength determined in advance and the outer surface temperature. In this case, even if measurement conditions such as the position of the imaging camera 20 and the state of the observation window 18 change, the change in brightness due to the change in measurement conditions can be canceled out using the brightness ratio between the first wavelength A and the second wavelength B, and an advantage of the estimated temperature not being easily affected is obtained. The first wavelength and the second wavelength are not limited, but may be, for example, 1 to 3 μm, which is a black body radiation wavelength at 1,000° C. to 1,300° C.

(3) In addition, a method in which a calibration curve is created using a frequency ratio of 3 or more and estimation is performed, or a method in which an outer surface temperature is estimated using a color video camera from the brightness and wavelength spectrums can be used.

OTHER EMBODIMENTS

In the example in FIG. 2, the imaging camera 20 is fixed by the platform 53, and the region to be imaged 60 is always constant. However, in another embodiment shown in FIG. 4, the imaging camera 20 can be rotated horizontally and vertically during imaging, and can scan the field of view 61 shown in FIG. 5. In the configuration in which the field of view 61 is scanned, a wider range than the field of view 61 of each imaging camera 20 can be imaged so that it is possible to increase the detection probability of the hotspot 62 and it is possible to predict the decoking time with higher accuracy.

Figure 4:
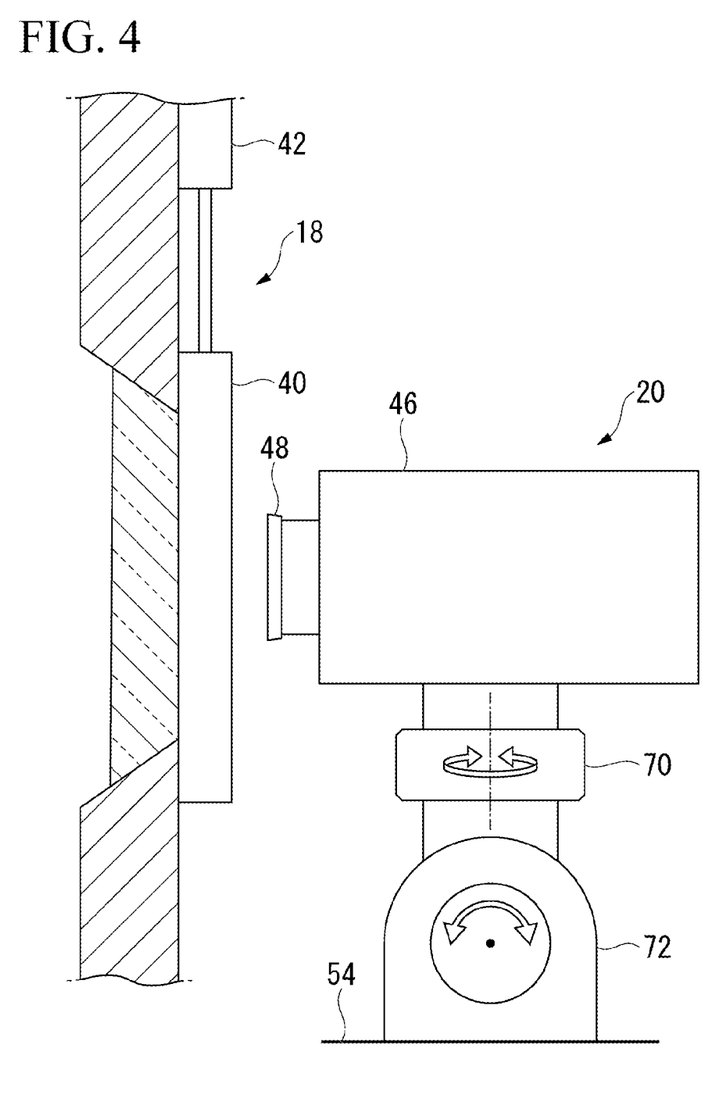
FIG. 4 is a side view showing an imaging camera according to another embodiment of the present invention.

In this example, a horizontal drive unit 70 that swivels the camera main body 46 horizontally in a certain angle range by an actuator and a vertical drive unit 72 that swivels the camera main body 46 vertically in a certain angle range by an actuator are provided, and the bottom of the vertical drive unit 72 is fixed to the support stand 54 installed in front of the observation window 18. It is possible to provide only one of the horizontal drive unit 70 and the vertical drive unit 72.

The actuator of the horizontal drive unit 70 and the actuator of the vertical drive unit 72 are each controlled by a computer program of a control system (not shown). This program drives the actuator 42 and opens the shutter 40 when imaging is performed, and starts imaging by the imaging camera 20, additionally drives the horizontal drive unit 70 and the vertical drive unit 72, and scans by moving the field of view 61 of the imaging camera up and down while reciprocating left and right over almost the entire area of the range in which the inside of the radiant section 8B is viewed through the transparent window 44. Therefore, even if the field of view 61 of the imaging camera 20 is narrowed, as shown in FIG. 3, the field of view 61 of the imaging camera 20 is scanned over almost the entire area of the region to be imaged 60 viewed from the transparent window 44, and the outer surface of the radiant coil 8B is imaged. After the measurement is completed, the imaging camera returns to the initial position, and the shutter 40 is closed. Therefore, even if the hotspot 62 occurs only in a part of any of the radiant coils 8B, it is possible to estimate the temperature of the hotspot 62.

Figure 5:
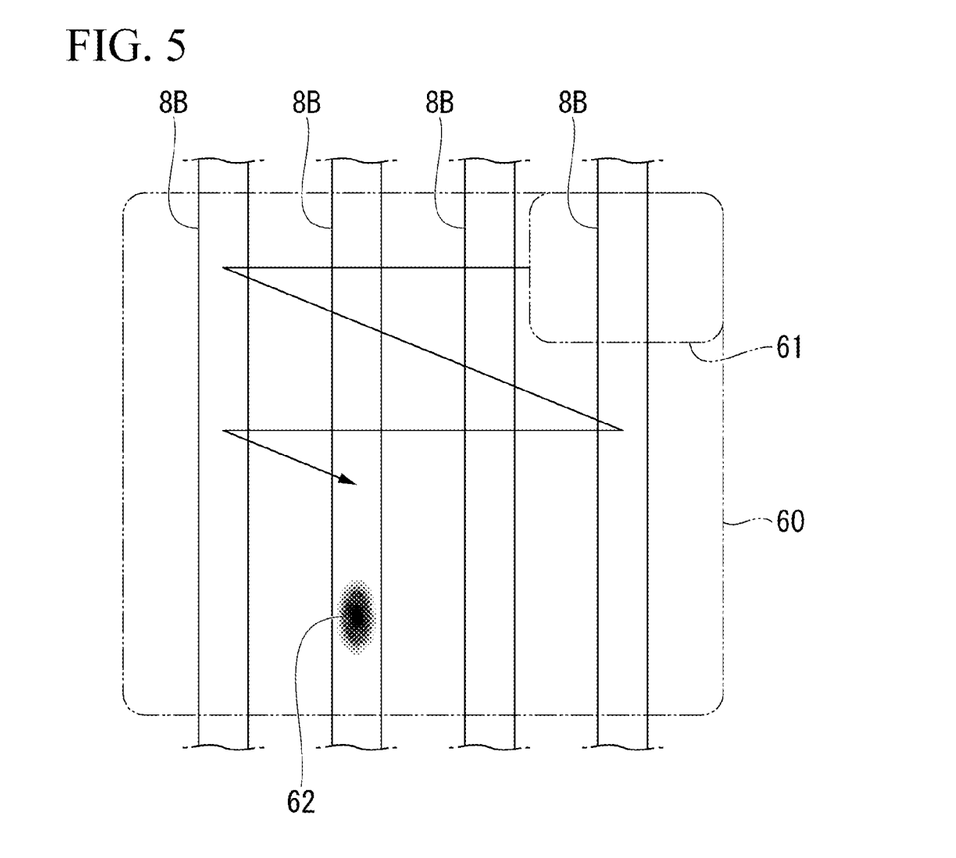
FIG. 5 is a front view showing a state in which a hotspot of a radiant coil is detected according to another embodiment.

The image analyzer 22 synthesizes the image imaged by the imaging camera 20 during scanning in a computer to generate one image, and for example, the position of the hotspot 62 occurring in the image may be displayed on the display device as shown in FIG. 5. The image may be an image obtained by simply stitching and synthesizing individual images imaged by the imaging camera 20, or may be an image that can be recognized as a temperature distribution in which the synthesized image is schematically processed. Therefore, it is possible to visually confirm a position at which a hotspot has occurred in a wide range of images of the radiant coil, and a trend can be understood by collecting hotspot appearance positions and appearance frequency information, and this can be effectively used as information for determining a decoking time and maintenance.

Alternatively, the image analyzer 22 may display the image imaged by the imaging camera 20 during scanning as a continuous video on the display device and display the occurrence position of the hotspot 62 and the video, which are superimposed. Even with this display format, it is possible to visually confirm a position at which a hotspot has occurred in a wide range of images of the radiant coil, and a trend can be understood by collecting hotspot appearance positions and appearance frequency information, and this can be effectively used as information for determining a decoking time and maintenance.

While embodiments of the present invention have been described above, the present invention is not limited to the above embodiments, and various modifications can be made within the scope of claims to be described below.

INDUSTRIAL APPLICABILITY

According to the method and device for estimating an outer surface temperature of a radiant coil of an cracking furnace for ethylene production according to the present invention, it is possible to predict a decoking time with high accuracy without relying on an operator, it is possible to perform decoking at an appropriate time, and it is possible to improve production efficiency of ethylene. Therefore, the present invention can be used industrially.

REFERENCE SIGNS LIST

1 Cracking furnace for ethylene production
2 Housing
3 Device for estimating outer surface temperature of radiant coil
4 Convection section
5 Communication section
6 Radiant section
8 Coil
8A Convection coil
8B Radiant coil
10 Steam introduction pipe
12 Delivery tube
14 Combustion nozzle
16 Nozzle hole
18 Observation window
20 Imaging camera
22 Image analyzer
40 Shutter
42 Actuator
44 Transparent window
46 Camera main body
48 Lens
50 Horizontal swivel unit
52 Vertical swivel unit
53 Platform
54 Support stand
60 Region to be imaged
61 Camera field of view
62 Hotspot
70 Horizontal drive unit
72 Vertical drive unit

What is claimed is:

1. A method for estimating an outer surface temperature of a radiant coil of a cracking furnace for ethylene production including a convection coil that preheats hydrocarbons as raw materials and steam, a radiant coil that thermally decomposes the preheated hydrocarbons and steam, and a housing for accommodating them, the method comprising:
a process in which a region to be imaged of the radiant coil is imaged by an imaging camera; and
a process in which an output signal from the imaging camera is processed by an image analyzer and an outer surface temperature of the imaged radiant coil is estimated,
wherein the imaging camera is a color video camera that outputs brightness for each light-receiving pixel at each wavelength of RGB, a monochromatic video camera that outputs brightness for each light-receiving pixel at a single wavelength of 1 to 3 µm, or a 2-sensor camera that outputs a brightness ratio between a first wavelength and a second wavelength, both of which are 1 to 3 µm.

2. The method for estimating the outer surface temperature of the radiant coil of the cracking furnace for ethylene production according to claim 1,
wherein the region to be imaged by the camera is a region of the radiant coil that spans a plurality of the radiant coils.

3. The method for estimating an outer surface temperature of the radiant coil of the cracking furnace for ethylene production according to claim 1,
wherein the image analyzer estimates a maximum temperature in the region to be imaged.

4. The method for estimating the outer surface temperature of the radiant coil of the cracking furnace for ethylene production according to claim 1,
wherein the image analyzer processes the output signal from the imaging camera, identifies a hotspot in the region to be imaged, and calculates a hotspot temperature in the hotspot.

5. The method for estimating the outer surface temperature of the radiant coil of the cracking furnace for ethylene production according to claim 1,
wherein the outer surface temperature of the radiant coil at any position estimated by the image analyzer is displayed on a display device together with the estimated position information.

6. A device for estimating an outer surface temperature of a radiant coil of a cracking furnace for ethylene production, which is provided in the cracking furnace for ethylene production including a convection coil that preheats hydrocarbons as raw materials and steam, a radiant coil that thermally decomposes the preheated mixed gas of hydrocarbons and steam, and a housing for accommodating them, the device comprising:
an imaging camera that images a region to be imaged of the radiant coil; and
an image analyzer that processes an output signal from the imaging camera and estimates an outer surface temperature of the radiant coil,
wherein the imaging camera is a color video camera that outputs brightness for each light-receiving pixel at each wavelength of RGB, a monochromatic video camera that outputs brightness for each light-receiving pixel at a single wavelength of 1 to 3 µm, or a 2-sensor camera that outputs a brightness ratio between a first wavelength and a second wavelength, both of which are 1 to 3 µm.

7. The device for estimating the outer surface temperature of the radiant coil of the cracking furnace for ethylene production according to claim 6,
wherein the region to be imaged by the imaging camera is a region of the radiant coil that spans a plurality of radiant coils.

8. The device for estimating the outer surface temperature of the radiant coil of the cracking furnace for ethylene production according to claim 6,
wherein the image analyzer includes a maximum temperature estimating unit that estimates a maximum temperature in the region to be imaged.

9. The device for estimating the outer surface temperature of the radiant coil of the cracking furnace for ethylene production according to claim 6,
wherein the image analyzer includes a hotspot identification unit that processes the output signal from the imaging camera and identifies a hotspot in the region to be imaged and a hotspot temperature calculation unit that calculates a hotspot temperature in the hotspot.

10. The device for estimating an outer surface temperature of the radiant coil of the cracking furnace for ethylene production according to claim 6,
wherein the outer surface temperature of the radiant coil at any position estimated by the image analyzer is displayed on a display device together with the estimated position information.

11. An ethylene producing device comprising the device for estimating the outer surface temperature of a radiant coil of an cracking furnace for ethylene production according to claim 6, comprising
a cracking furnace for ethylene production including a convection coil that preheats hydrocarbons as raw materials and steam, a radiant coil that thermally decomposes the preheated mixed gas of hydrocarbons and steam, and a housing for accommodating them.

12. The device for estimating the outer surface temperature of the radiant coil of the cracking furnace for ethylene production according to claim 6, further comprising:
a horizontal drive unit that swivels the imaging camera horizontally,
a vertical drive unit that swivels the imaging camera vertically, and
a control system that controls the horizontal drive unit and the vertical drive unit so as to scan a field of view of the imaging camera by moving the field of view up and down while reciprocating the field of view left and right,
wherein the image analyzer estimates the outer surface temperature of the radiant coil by processing the output signal of images captured during scanning the field of view of the imaging camera.

* * * * *